United States Patent [19]
Schoenen et al.

[11] Patent Number: 5,473,943
[45] Date of Patent: * Dec. 12, 1995

[54] ULTRASONIC TEST DEVICE

[75] Inventors: Manfried Schoenen, Mettmann; Harri Haacke, Ratingen-Vokarday; Hans-Jürgen Bäthmann, Moers; Bernhard Karbach, Erfstadt-Friesheim; Gerd Kauth, Köln; Reinhard Prause, St. Augustin; Ottokar Patzke, Erfstadt-Liblar, all of Germany

[73] Assignees: Mannesmann Aktiengesellschaft, Dusseldorf; Krautkramer GmbH & Co., Mettmann, both of Germany

[*] Notice: The portion of the term of this patent subsequent to Jul. 20, 2010, has been disclaimed.

[21] Appl. No.: 977,422

[22] PCT Filed: Aug. 16, 1991

[86] PCT No.: PCT/DE91/00658

§ 371 Date: Feb. 17, 1993

§ 102(e) Date: Feb. 17, 1993

[87] PCT Pub. No.: WO92/03725

PCT Pub. Date: Mar. 5, 1992

[30] Foreign Application Priority Data

Aug. 17, 1990 [DE] Germany .......................... 40 26 458.0
Aug. 13, 1991 [DE] Germany .......................... 91 10 160 U

[51] Int. Cl.⁶ .................................................. G01N 29/00
[52] U.S. Cl. .................................................. 73/644; 73/635
[58] Field of Search ........................... 73/644, 635, 628, 73/622

[56] References Cited

U.S. PATENT DOCUMENTS

| 2,873,391 | 2/1959 | Schulze | 73/644 |
| 3,382,707 | 5/1968 | Haselwood | 73/644 |
| 3,868,847 | 3/1975 | Gunkel . | |
| 4,712,428 | 12/1987 | Ishii et al. | 73/644 |
| 4,899,590 | 2/1990 | Light . | |
| 4,907,455 | 3/1990 | Lawrie . | |
| 5,062,301 | 11/1991 | Aleshin et al. | 73/635 |
| 5,228,343 | 7/1993 | Schoenen et al. | 73/644 |

FOREIGN PATENT DOCUMENTS

| 71 28539 | 3/1972 | France | G01B 13/00 |
| 27 40 106.5 | 3/1979 | Germany | G01N 29/04 |
| 28 40 456.0 | 3/1980 | Germany | G01N 29/04 |

Primary Examiner—Richard Chilcot
Assistant Examiner—Ronald Biegel
Attorney, Agent, or Firm—Cohen, Pontani, Lieberman & Pavane

[57] ABSTRACT

The invention is directed to a u/s test device for nondestructive testing of a workpiece moving relative thereto by the pulse echo method, having a fluid coupling between the ultrasonic oscillator and the surface of the work material. At least two test heads are provided whose sound beam axes intersect at a point in the region of the workpiece and a travel path in the form of a chamber is provided for guiding the fluid medium. To reduce susceptibility to interference and to achieve high test performance, a separately guided travel path extending along a determined length of the chamber and forming a duct (12–20) is associated with each test head (1–9), the axes of the travel path being aligned with the respective sound beam axis.

12 Claims, 9 Drawing Sheets

ULTRASONIC TEST DEVICE

BACKGROUND OF THE INVENTION

1. Field of the Invention

The invention is directed to an ultrasonic or u/s test device for nondestructive testing of a workpiece moving relative thereto by the pulse echo method.

2. Description of the Prior Art

DE-OS 27 40 106 discloses a u/s test device for nondestructive testing of metallic objects having a test head carrier at which are arranged three test heads whose sound beam axes intersect at a point on the inside of the workpiece and which are outfitted with fluid coupler systems for coupling with the workpiece surface. The test heads are fastened so as to be adjustable at the carrier frame at a distance from one another and a travel path forming a duct is associated with each test head separately. The two outer test heads work according to the pulse echo system, wherein one test head functions as the transmitter and the other functions as the receiver. Since the intensity of the received signal is highly dependent on the surface geometry, the alignment of the two outer test heads corresponding to the surface geometry of the workpiece to be tested must be effected by the third test head arranged between the two outer test heads by means of a sound attenuation measurement.

A disadvantage in this test device consists in that it is restricted to only one type of acoustic irradiation and in the costly electronics required for optimally adjusting the transmitting and receiving test heads. Further, signal processing required for the adjustment of the test heads puts a strain on the testing performance.

A u/s test device for nondestructive testing of welds is known from DE-OS 27 51 810 in which a total of six test heads, whose sound beams intersect at a point, are arranged in a test spider. The sound-transmitting coupling is effected by guiding water into the contact plane. A disadvantage in this arrangement consists in that the coupling medium is supplied to the test device in an uncontrolled manner and the cost for controlling the coupling is accordingly very high. Further, the test performance is very low due to the cyclical interrogation of the individual test heads, since it is always necessary to wait for the echo of the radiated sound pulse first before the next sound pulse can be radiated. Another substantial disadvantage consists in that the test heads are installed in individual holders which change position relative to one another due to tolerances of the test piece or transporting and guidance tolerances.

SUMMARY OF THE INVENTION

The object of the present invention is to provide an improved u/s test device with which testing can be carried out at a high performance level extensively without being susceptible to interference. A further object consists in that the u/s test device is constructed in such a way that it can be adapted simply and quickly to different test jobs and shapes as well as to acoustic characteristics of the test piece and is particularly suitable for pipe testing.

This object is achieved by providing an ultrasonic test device for the nondestructive testing of a workpiece moving relative thereto, based on the pulse echo method with coupling by means of a fluid medium between the ultrasonic oscillator and the surface of the workpiece, said ultrasonic test device comprising: a first test head carrier; at least two test heads disposed in said carrier, each said test head having a sound beam axis, said axes intersecting at a point in the region of the workpiece; a chamber common to all test heads for guiding the fluid medium, said chamber having an outlet opening facing the surface of the workpiece and being connected with said test head carrier; a guide element constructed so as to correspond to the contour of the workpiece and being connected with said test head carrier; and a separate travel path formed by a duct (12–20) associated with each of said test heads (1–9), each said separate travel path having an axis and extending along a determined length of said common chamber, the axis of each of said travel paths being aligned with a respective one of said sound beam axes.

This object is achieved by providing an ultrasonic test device for the non destructive testing of a workpiece moving relative thereto, based on the pulse echo method with coupling by means of a fluid medium between the ultrasonic oscillator and the surface of the workpiece, said ultrasonic test device comprising: a first test head carrier; at least two test heads disposed in said carrier, each said test head having a sound beam axis, said axes intersecting at a point in the region of the workpiece; a chamber common to all test heads for guiding the fluid medium, said chamber having an outlet opening facing the surface of the workpiece and being connected with said test head carrier; a guide element constructed so as to correspond to the contour of the work piece and being connected with said test head carrier; and a separate travel path forming a duct (12–20) associated with each of said test heads (1–9), each said separate travel paths having an axis and extending along a determined length of said common chamber, the axis of each of said travel paths being aligned with a respective one of said sound beam axes.

The ultrasonic device may further comprise a second test head carrier including additional test heads disposed immediately adjacent to said first test head carder, the sound beams of said test heads of said first and second test head carriers having, relative to the workpiece, opposite acoustic irradiation directions. Preferably, a total of nine test heads are arranged in the first test head carder, so that a test head is arranged in the center and eight additional test heads are arranged at a distance to the center test head so as to be symmetrically distributed along a circle with an offset of 45°. More preferably, the test head arranged in the center is utilized and constructed for testing the wall thickness and lamination. The ultrasonic device preferably comprises a holder for holding the test head carder in a manner of a cardan joint when testing a pipe. A guide element having at least two prismatically constructed wear bases is arranged to the right and left at the same distance next to the test axis of the device and is adjustable transversely relative to the axis of the pipe. A rolling bearing is arranged in the wear base in such a way that the axis of the rolling bearing lies parallel to the axis of the pipe and a portion of the outer circumference projects over the wear surface of the base facing the pipe.

The guide element may also have two rotatory supported rollers disposed in a receiving part. The rollers are fastened on the fight and left sides next to the test axis of the device at a fixed distance from one another and their axes are lying parallel to the axis of the pipe when the pipe moves in a helical line along the stationary test head carrier.

The ultrasonic device preferably comprises an exchangeable intermediate layer arranged between the receiving part and the holder.

The guide element may also comprise a member constructed in a sickle-shaped member in cross section and the tips of the sickle are located in the region of the outlet edge of the exchangeable insert and enclose the outlet opening of the exchangeable insert and the surface facing the pipe is curved corresponding to the outer surface area of the pipe and the region of the exchangeable insert adjoining the outlet opening and the bushing are covered by the sickle-shaped member when the pipe moves in a helical line along the stationary test head carrier. The guide element may additionally comprise rolls or rollers arranged to the fight and left adjacent to the sickle-shaped member.

The test head is preferable guided in a bushing which is inserted and fixed in the bore hole of a holding plate and whose end facing the test piece is constructed so as to be spherical.

Finally, the ultrasonic device may additionally comprise a displacement plate disposed parallel below the holding plate and wherein the displacement plate is displacably arranged on the test head carder and has a bore hole suitable for the test head to pass therethrough. The end of the bore hole facing the holding plate is constructed so as to be spherical and the test head carrier and the displacing plate have elongated holes which are constructed so as to be adapted to the predetermined adjustment path and are aligned radially relative to the center of the test head carrier.

The ultrasonic device may further comprise a second test head carrier including additional test heads disposed immediately adjacent to said first test head carrier, the sound beams of said test heads of said first and second test head carriers having, relative to the workpiece, opposite acoustic irradiation directions. Preferably, a total of nine test heads are arranged in the first test head carrier, so that a test head is arranged in the center and eight additional test heads are arranged at a distance to the center test head so as to be symmetrically distributed along a circle with an offset of 45° (i.e. at intervals of 45°). More preferably, the test head arranged in the center is utilized and constructed for testing the wall thickness and lamination. The ultrasonic device preferably comprises a holder for holding the test head carrier in a manner of a cardan joint when testing a pipe. A guide element having at least two prismatically constructed wear bases is arranged to the right and left at the same distance next to the test axis of the device and is adjustable transversely relative to the axis of the pipe. A rolling bearing is arranged in the wear base in such a way that the axis of the rolling bearing lies parallel to the axis of the pipe and a portion of the outer circumference projects over the wear surface of the base facing the pipe.

The guide element may also have two rotatory supported rollers disposed in a receiving part. The rollers are fastened on the right and left sides next to the test axis of the device at a fixed distance from one another and their axes are lying parallel to the axis of the pipe when the pipe moves in a helical line along the stationary test head carrier.

The ultrasonic device preferably comprises an exchangeable intermediate layer arranged between the receiving part and the holder.

The guide element may also comprise a member constructed in a sickle-shaped member in cross section and the tips of the sickle are located in the region of the outlet edge of the exchangeable insert and enclose the outlet opening of the exchangeable insert and the surface facing the pipe is curved corresponding to the outer surface area of the pipe and the region of the exchangeable insert adjoining the outlet opening and the bushing are covered by the sickle-shaped member when the pipe moves in a helical line along the stationary test head carrier.

The guide element may additionally comprise rolls or rollers arranged to the right and left adjacent to the sickle-shaped member.

The test head is preferably guided in a bushing which is inserted and fixed in the bore hole of a holding plate and whose end facing the test piece is constructed so as to be spherical.

Finally, the ultrasonic device may additionally comprise a displacement plate disposed parallel below the holding plate and wherein the displacement plate is displaceably arranged on the test head carrier and has a bore hole suitable for the test head to pass therethrough. The end of the bore hole facing the holding plate is constructed so as to be spherical and the test head carrier and the displacing plate have elongated holes which are constructed so as to be adapted to the predetermined adjustment path and are aligned radially relative to the center of the test head carrier.

It is substantial to the invention that the central duct of the chamber guiding the fluid medium is divided into a plurality of separate ducts. The number of ducts corresponds to the number of test heads provided and the axes of the ducts are aligned with the respective sound beam axis of the test head. Stray sound pulses are extensively suppressed in that a separate travel path is formed for each test head in the form of a duct extending along a determined length of the chamber and guiding the fluid medium. The acceptable signal-to-noise ratio can accordingly be substantially improved and a higher pulse repetition frequency can be used in general. Further, the coupling ratios can be improved by means of the separate travel paths since the guidance of the coupling medium is improved. In order to enhance the rapid and simple adaptation to different test jobs, the chamber is constructed as a bushing in which an insert provided with the ducts guiding the fluid medium is arranged. This makes it possible to manufacture different inserts beforehand which can then be adapted to different test jobs with respect to the cross section and inclination of their ducts. It has proven particularly advantageous to produce the insert from Teflon. The acoustic characteristics of this work material are similar to those of water so that unwanted overcoupling in the duct is prevented.

The number and arrangement of test heads in the test head carrier is optional within certain limits. One limit is imposed by the need to keep the test head carrier as small as possible for reasons of convenience so that it can also be used as a rotation head e.g. when testing pipes or rods. The other limit results from the given geometry of the selected oscillator size and physical characteristics such as frequency and near field length.

At least two test heads are arranged in a first simple embodiment form. This embodiment form corresponds in principle to two separately working test heads with the distinction that the sound beams intersect at a point in the region of the workpiece. This is advantageous in that all obtainable information originates from one and the same location and no electronics are necessary for correlating the received signals of the individual test heads with respect to actual respective location.

To meet international testing regulations, it is also necessary to test in the opposite acoustic irradiating direction so as to ensure that a defect whose reflection surface is unfavorably situated with respect to the original acoustic irradiating direction can also be noticed. This can be realized in a simple manner by arranging an additional test head carrier immediately adjacent to a first test head carrier. In so doing, the acoustic irradiating direction of the arranged test heads would be opposed to that of the first test head carrier. All known testing requirements can be met with such an arrangement and a parallel operation of all test heads would be possible. A disadvantage consists in that the cost on apparatus is relatively high since two separate test head carriers must be precisely adjusted and supported and the resulting two test locations are widely separated, which again requires expenditure on electronic correlating apparatus.

For this reason it is suggested that a total of nine test heads preferably be arranged in a test head carrier. With the exception of the test head arranged in the center, the remaining eight test heads are arranged in a circular or star-shaped manner around the central test head so as to be offset by 45° in each instance. In this arrangement, for example, the test heads are divided up into one pair of test heads for longitudinal defect testing, one for transverse defect testing and two pairs of test heads for diagonal defect testing. The test head arranged in the center is preferably used for testing wall thickness and lamination. It also serves as a coupling control at the same time. In this arrangement the two cooperating test heads lie exactly opposite one another in all test head pairs. This is advantageous in that there is only one common test location for all test heads so that the former customary expenditure on electronics for correlating the occurring signals with respect to actual respective location can be dispensed with. The common test location can be situated optionally on the outer surface of the test piece or on the rear wall. The first variant has the advantage that testing does not depend on the dimensions of the test piece within a wide range. However, this range is limited by the relative refraction coefficients of the ultrasound in the workpiece, since the usable sound beam lobe no longer extends to the rear wall after a certain thickness is reached. The sound beam angle must then be changed in order to test workpieces having a thicker wall. As an alternative, it is also possible to situate the common test location on the rear wall. This has the disadvantage that a different adjustment is required for every thickness. Therefore, this adjustment of the test location is always only applied when testing large batches which always have the same dimensions. The advantage of the latter adjustment of the test location consists in that unfavorably situated internal defects can also be reliably detected with high probability. It may be advisable in certain test jobs to arrange the common test location in the region extending through the thickness of the workpiece, i.e. between the outer surface and rear wall.

A precise adjustment of the sound field lobe of the test heads is facilitated in that the test heads are fastened in the test head carrier so as to be adjustable in the axial direction. Further, by using corresponding eccentric bushings which can be inserted in the test head carrier, it is possible to compensate extensively for the given squint of the test head by rotating the bushing. Another possibility to compensate for squint consists in constructing the end of the bushing facing the test piece so as to be spherical. The through-bore hole in the test head carrier for the individual test heads is likewise constructed in a spherical manner on the side remote of the test piece so as to form a ball joint in combination with the bushing arranged on the opening. The test head can be tilted toward any side within a small range by variously tightening the holding plate holding the bushing by means of three screws so that the sound beam axes can be exactly adjusted. The sound angle can also be changed slightly with this method, i.e. approximately to a maximum of 3/4°. However, this type of angular adjustment is very complicated since the ability to tilt the bushing support entails the risk that the common test location will be shifted simultaneously while the angle is being adjusted. Another possibility is that excessive adjustment will cause the sound field lobe to brush the wall of the duct guiding the water and trigger reflections. The reason for this is that the center of rotation of the adjustment is situated in the plane of the spherical guide and is offset relative to the common test location.

When using the u/s test device according to the invention for test pieces having different acoustic characteristics it cannot be ruled out that the sound beam angle which is set once in a definite manner beforehand will not be optimal for one test piece or another. The slight adjustability of the test head described above also does not alter this problem. Therefore, to solve this problem it is suggested in a further development to arrange a displacing plate below and parallel to the holding plate so that it is displaceable relative to the test head carrier. Ideally, the displacing plate must move on a circular path so as to maintain the common test location. However, this would mean that the displacing plate and the corresponding region on the adjusting body would have to be constructed in a spherical manner. However, the manufacturing cost required for producing such spherical surfaces is very high and accordingly the cost of such a test device would also be high. It is simpler to compensate for the corresponding surface on the adjusting body with linear deviation resulting from the tangential, rather than circular, displacement with respect to the common test location by constructing the bushing guiding the test head in a spherical manner as already described. In order to enable the angular adjustment of all test heads arranged on a circle the elongated holes provided for this purpose in the displacing plate and in the adjusting body are aligned radially relative to the center of the test head carrier. The angular adjustment enabled by this displacement is in the range of ±1.5°. This is advantageous in that a sound angle resulting in an optimal acoustic irradiating angle of 45° in the workpiece can also be predetermined in extreme cases. When using the test head carrier according to the invention for testing pipe, the device is arranged in a holder in the manner of a cardan joint so that it can be adapted to the curvature ratios in a simple manner. Further, the known prismatically constructed wear bases are connected with the test device so as to be displaceable transversely relative to the axis of the test piece. This makes it easier to adapt the guide mechanism to different diameters of pipes to be tested. In a stationary test head carrier, the pipe would move along a helical line to ensure complete coverage. Alternatively, the pipe can also move without rotation around its longitudinal axis when the test head carrier rotates around the pipe. The disadvantage of providing wear bases as a guide element consists in that the bases must be changed relatively frequently after continuous operation, particularly in the case of hot-finished pipes. For this reason, it is suggested in a further development to cut a transverse groove into the bases and arrange a roller bearing in a cantilevering manner. The arrangement is selected in such a way that the axis of the roller bearing lies parallel to the pipe axis and a portion of the circumferential surface of the roller bearing projects over the wear surface of the base facing the pipe. The base accordingly only assumes the function of a supporting body for the roller bearing since the base itself is no longer supported on the pipe body. Since the roller bearing is produced from hardened steel, it has a considerably longer useful life compared with the base which is manufactured from plastic. Another guiding possibility consists in arranging two rollers situated at a fixed distance from one another adjacent to the test axis of the device on the right and left sides. The points of support of the rollers on the pipe and the common test location form a triangle whose height depends on the curvature of the pipe. The height which changes as the pipe diameters change must be compensated for so that the water gap in the region of the test location remains constant. To this end, an exchangeable intermediate layer whose thickness corresponds to the change in height is arranged between the receiving part for the rollers and the holder at the test head carrier.

All guides working with elements which are in contact with the moving pipe surface are subject to wear. Therefore, a non-contacting guidance would be ideal, e.g. in the manner of a floating support making use of the aquaplaning effect. To this end, it is suggested to provide a sickle-shaped member whose sickle-shaped tips lie in the region of the outlet edge of the chamber and enclose the outlet opening. The surface of the element facing the pipe surface is correspondingly curved. A narrowly defined gap is accordingly formed between the pipe surface and test head and the water flowing out of the chamber is pressed through this gap. With a corresponding pipe rotation and supply of water the test head aquaplanes or floats and is guided without making contact. A precondition for this consists in that the pipe surface be correspondingly smooth and planar, e.g. as in a drawn or cold-rolled precision pipe. Another precondition would be that the dimensions not be changed too frequently, since a correspondingly curved sickle-shaped member is required for every diameter. The additional guidance by means of rolls or rollers is indispensable when testing hot-finished pipes, since the supporting water wedge can sometimes collapse due to the unevenness of the surface. However, the effect is also advantageous in this case since the contacting guide elements can be relieved by the supporting water wedge and their useful life is accordingly increased. The gap on the outlet side which guides the water has the additional advantage that it suppresses the otherwise common whirling of the exiting water particularly in the longitudinal direction of the pipe and the signal-to-noise ratio is accordingly improved.

BRIEF DESCRIPTION OF THE DRAWINGS

The device according to the invention is explained in more detail in the drawing in which.

Detailed Description of the Presently Preferred Embodiments

Figure 1:
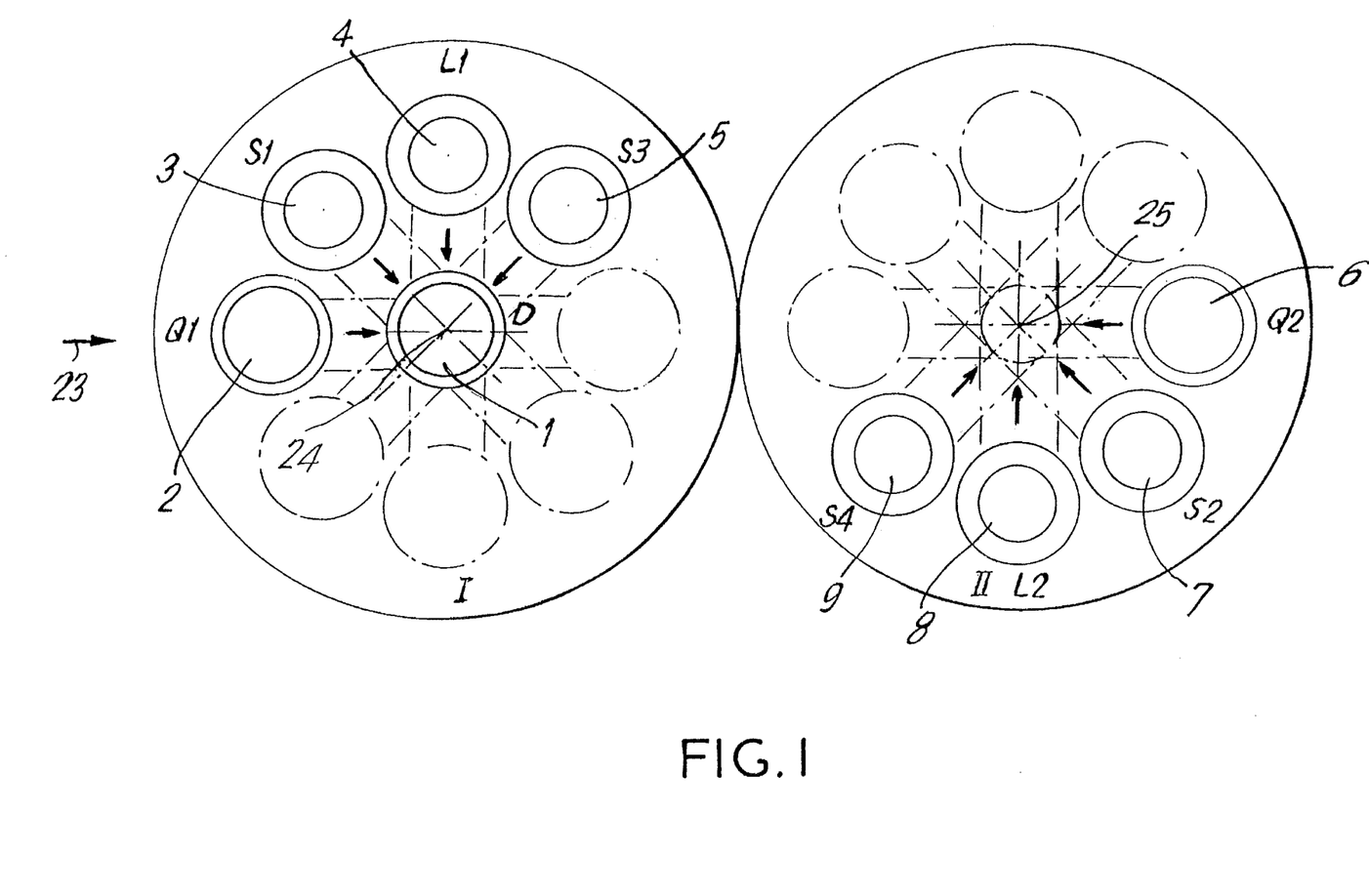
FIG. 1 is a schematic top view of the arrangement of two test head carriers I, II with a common test location and the corresponding oppositely located sound damping bore holes.
Figure 2:
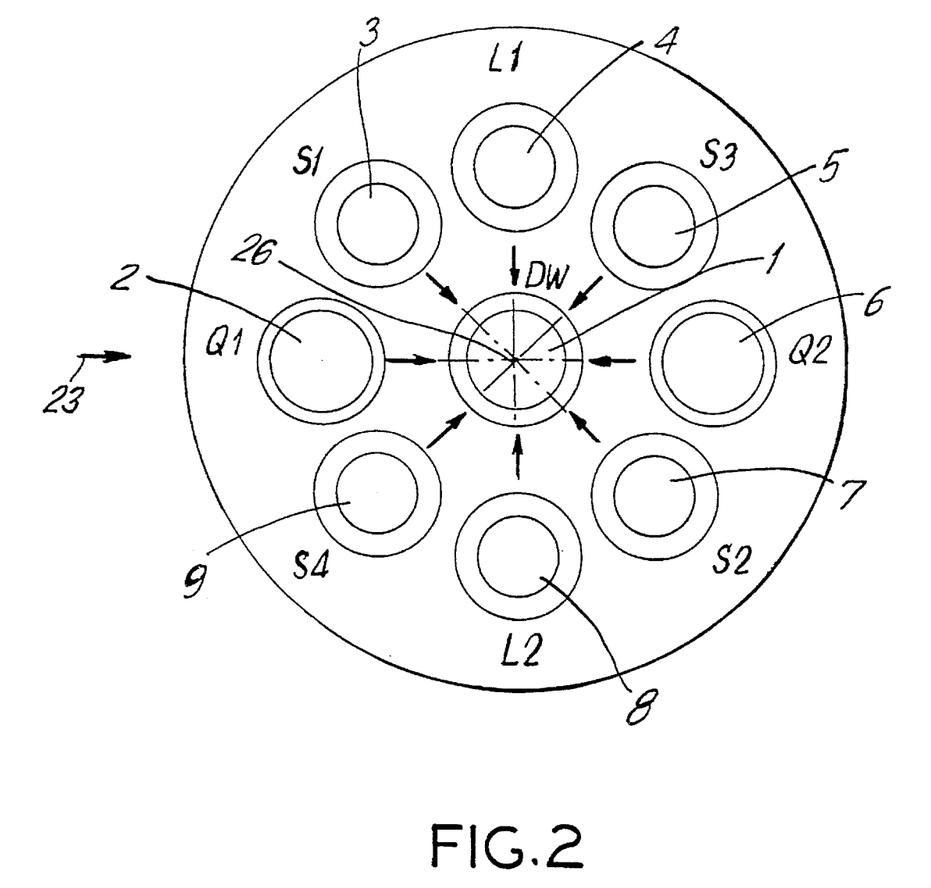
FIG. 2 is a schematic top view of a circular test head carrier with nine test heads.

The arrangement of two separate test head carriers I, II is shown schematically in FIG. 1 as seen from above. In FIGS. 1 and 2, the following abbreviations are used for the function of the individual test heads 1 to 9 and their sound damping bore holes which are located opposite:

DW=testing of lamination and wall thickness (vertical acoustic irradiation)

Q1, Q2=transverse defect testing

L1, L2=longitudinal defect testing

S1–S4=diagonal defect testing

The feed direction of the workpiece, not shown in the drawing, is designated by the thick arrow 23. Only one test head carrier having a total of three test heads 1, 2, 4 or even only two test heads 2, 4 with the respective sound damping bore holes is provided in a first construction. The workpiece can be tested in only one acoustic irradiating direction with this construction, e.g. with respect to longitudinal and transverse defects, and with the addition of the test head 1 arranged in the center for testing wall thickness and lamination. Further, this test head 1 could additionally take over the function of coupling control. In an expanded construction, at least one more test head would be added for diagonal defect testing. If two additional test heads 3, 5 were arranged for diagonal defect testing this would correspond to the test head carrier I shown in FIG. 1. A characteristic of this test head carrier I consists in that the sound beams (symbolized here by the arrows proceeding from the test heads) intersect at only one point 24 (test location) and, with the exception of the test head 1 arranged in the center for testing lamination and wall thickness, the remaining four test heads 2–5 are arranged on a circle at a distance from the central test head 1. Parallel operation is possible since the sound beams of the test heads 2 to 5 do not influence one another with diagonal acoustic irradiation and inherent interference is prevented by the sound damping duct located opposite each test head 2, 3, 4, 5. However, such a test head carrier I can only be used if allowed by applicable test regulations and if the position and type of defect occurring most frequently is known fairly precisely. The internationally known test regulations prescribe acoustic irradiation in two opposite directions for reliable detection of workpiece defects. This requirement can be fulfilled in that the first test head carrier I is rotated by 180° and the workpiece must pass through this test head carrier I at least once. This problem can be solved in a somewhat more elegant manner by arranging an additional test head carrier II having a comparable arrangement of test heads 6–9 next to the first test head carrier I. This differs from the first test head carrier I in that the acoustic irradiating directions of the test heads are opposed. The sound beams of the test heads 6–9 of the second test head carrier II are aligned in a bundled manner comparable to those of the first test head carrier I so that a common intersecting point 25 (test location) is likewise formed, whose distance from the first intersecting point 24 of the first test head carrier I amounts to at least the diametrical length of the test head carrier.

An advantage of this construction consists in that the test heads 1–5 or 6–9 of each test head carrier I, II can be operated in parallel since the sound beams have no reciprocal influence. A disadvantage consists in the cost of the required mechanism for holding two test head carriers I, II and adjusting them to a common axis. Another disadvantage consists in that the two intersecting points 24, 25 of the widely separated sound beams require a corresponding correlation of the received signals with respect to actual respective location.

As a result of this disadvantage, the embodiment form shown in FIG. 2 is suggested. A total of nine test heads 1–9 are arranged in an individual test head carrier in this embodiment form. The sound beams of all test heads 1–9 are aligned in such a way that only one intersecting point 26 (test location) is formed which is optionally situated on the outer surface or on the rear wall of the workpiece to be tested. In this arrangement, the test heads form pairs which are located opposite one another while performing the same test function and whose sound beams are opposed. For example, the test heads 4, 8 form a test head pair for longitudinal defect testing, wherein the test head 8 on the right as seen in the feed direction 23 radiates sound in the counterclockwise direction and the test head 4 on the left radiates sound in the clockwise direction. An advantage of this arrangement consists in the possibility of a compact construction of the test head carrier so that the holding frame and guide take up little space. Further, it can also be used as a rotating test head in this compact form. Only one common intersecting point 26 (test location) is formed so that all information originates from one and the same location and a correlation with respect to actual respective location is not required. A disadvantage consists in that a disruptive influence of the sound beams of opposite test heads cannot be avoided so that parallel operation of all test heads is generally impossible. This problem can be solved by using the multiplex process. But the aimed for high pulse repetition frequency must be reduced in a corresponding manner in view of the testing capacity.

It should be emphasized with respect to the test head carriers shown in FIGS. 1 and 2 that the selected arrangement of the test heads and their association with a specific test function are only examples. A number of other combinations are possible without departing from the protective scope of the invention.

Figure 3:
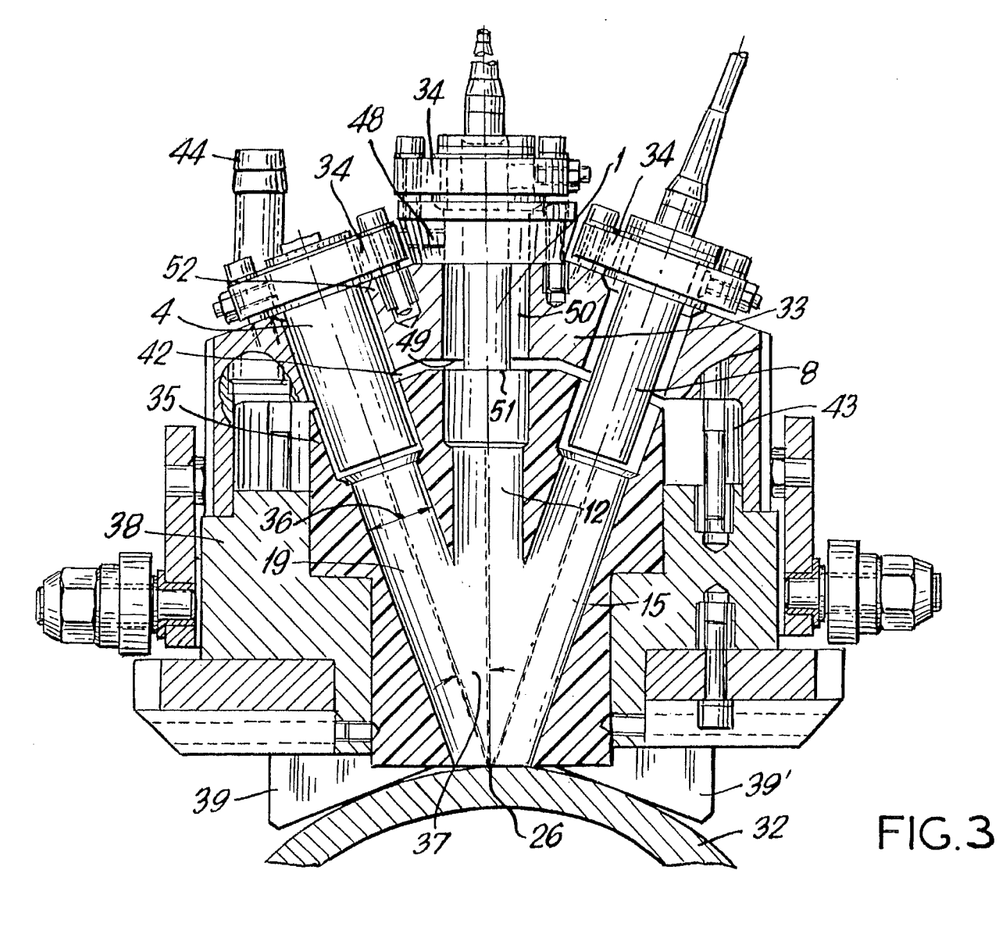
FIG. 3 is a cross sectional view through an embodiment example of a test device according to the arrangement shown in FIG. 2.
Figure 4:
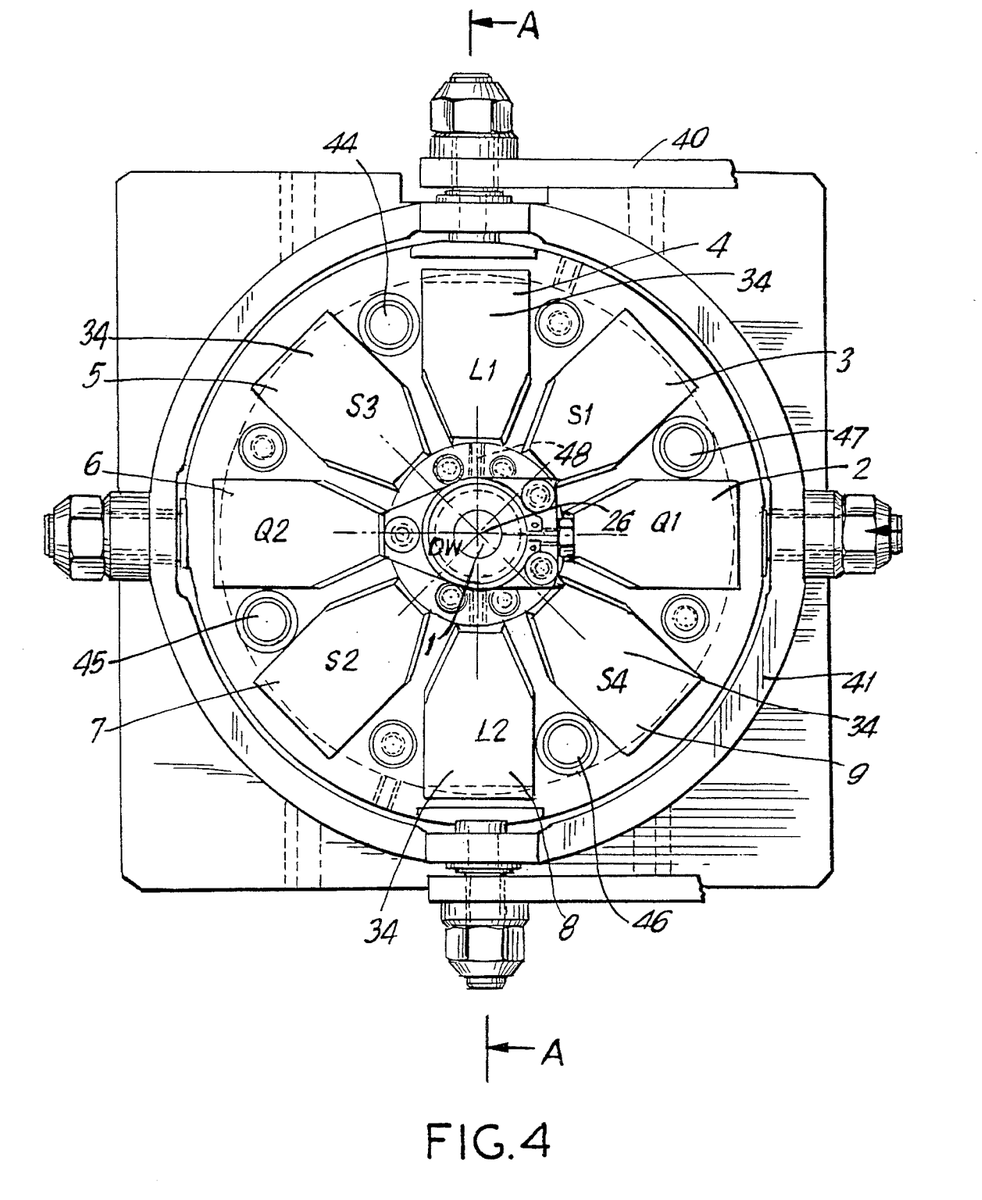
FIG. 4 is a top view of the test head carrier of FIG. 3.

The test device according to the invention in the arrangement shown schematically in FIG. 2 is shown in section in FIG. 3 and in a top view in FIG. 4. A pipe 32 is tested in the 12 o'clock position by way of example. The test can also be simulated e.g. in the 3, 6 or 9 o'clock positions by rotating the drawing. The test device includes a test head carrier 33 in which a total of nine test heads 1–9 are arranged in the arrangement shown schematically in FIG. 2. These test heads 1–9 are fastened in the test head carrier 33 via holding plates 34 in such a way that they can be fixed axially at different depths. Further, the axial direction of the test heads 1–9 can be corrected within certain limits, so that the axes of the sound beams (indicated here in dashed lines) are exactly aligned with the axes (indicated here as dash-dot lines) of the ducts 12–20. To this end, a bushing 52 is inserted and fixed in a bore hole of the holding plate 34; the end of the bushing 52 facing the test piece 32 is constructed in a spherical manner. Together with the corresponding spherical construction of the opening of the through-bore holes in the test head carrier 33, which opening is remote of the test piece 32, a kind of ball joint is formed which enables the test heads 1–9 to tilt toward all sides for the purpose of a sensitive adjustment. In particular, this adjusting possibility is used to compensate for the squint of the test heads. A duct 12–20 guiding the fluid medium is associated with each test head 1–9 according to the invention. In this embodiment example, the ducts 12–20 are cylindrical bore holes. The ducts 12–20 are arranged in an exchangeable insert 35 so that the test device can be adapted to different test jobs in a simple manner. Accordingly, the cross-sectional shape, the diameter 36, as well as the axial angularity 37, which amounts to 19 degrees in this example, can be varied. This insert is advantageously manufactured from Teflon, since this work material has acoustic characteristics similar to water. The insert 35 is held by a bushing 38 which is securely connected with the test head carrier 33. The guide mechanism, which in the case of pipe testing has two adjustable, prismatically constructed bases 39, 39', is arranged at the underside of the bushing 38. For the purpose of an exact adjustment of the test device when testing workpieces having curved surfaces, the test head carrier 33 together with the insert 35 fastened thereto and the bushing 38 is mounted in a frame 40, 41 in the manner of a cardan joint.

To ensure a reliable guidance of the fluid medium, the insert 35 is arranged relative to the test head carrier 33 in such a way that a gap 42 is formed in the connecting area. This gap 42 is constructed in the manner of a dome in this embodiment example and extends along all inlet openings of the ducts 12–20. In the area of the edge zones, the gap 42 expands to form an annular space 43 into which the connection ducts 44–47 open for supplying the fluid medium. A venting duct 48 is arranged at the highest point of the gap 42 or generally at the greatest distance from the surface of the workpiece. In order to make the test device universally usable for all clock hand positions, additional venting bore holes (not shown here) are arranged in the test head carrier 33 which can be opened or closed optionally. In order to avoid an accumulation of air bubbles in the region of the test heads 1–9 if possible, the test heads 1–9 are fastened in the test head carrier 33 in such a way that the end face of the test heads 1–9, for example, 51 of the central test head 1, projects beyond the outlet surface 49 of the bore hole 50, but at least terminates so as to be flush with it. In the two other test heads 4, 8 shown here, the end face even projects far into the respective duct 15, 19 of the insert 35.

Figure 5:
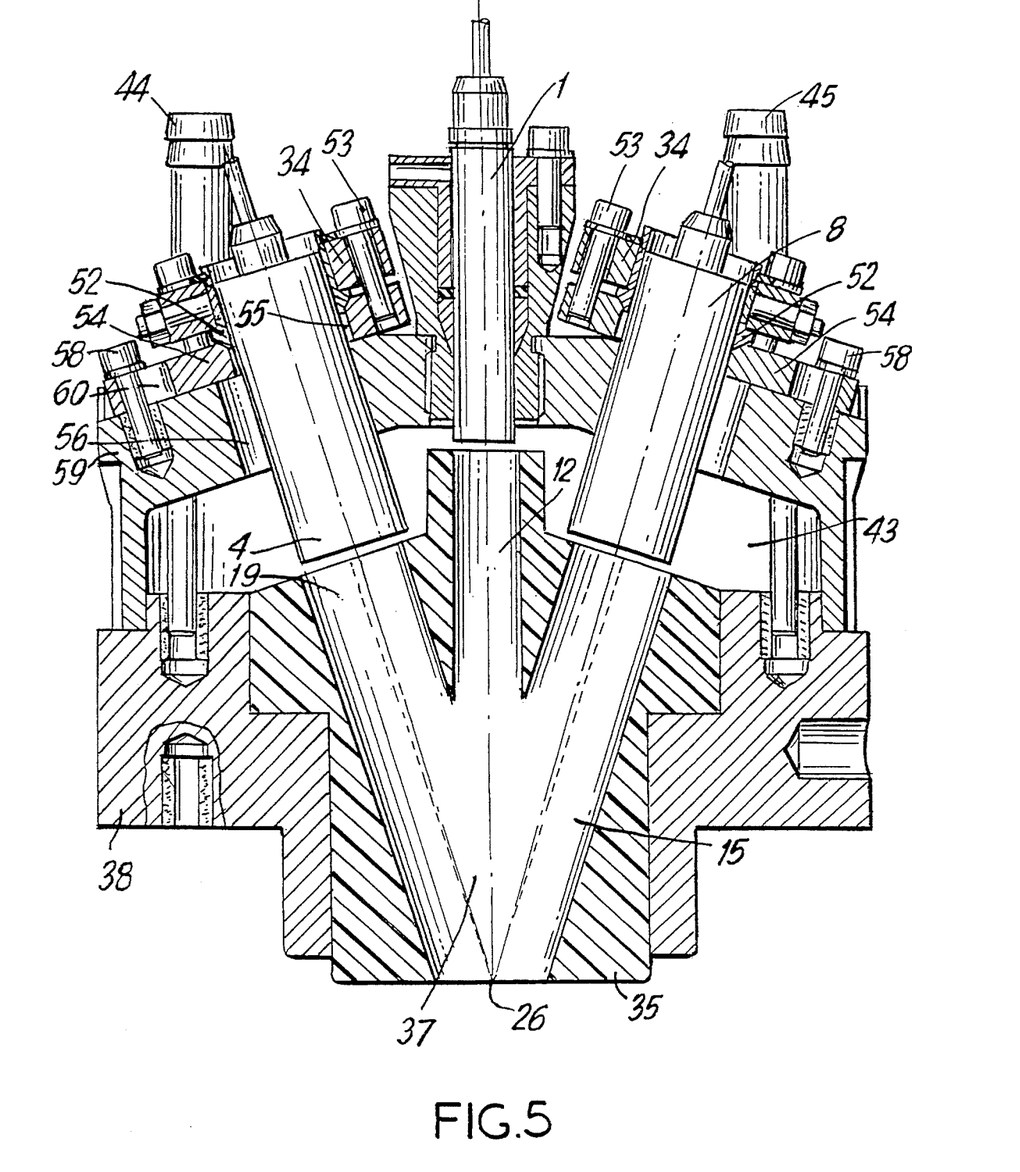
FIG. 5 shows another embodiment example in the same way as in FIG. 3.
Figure 6:
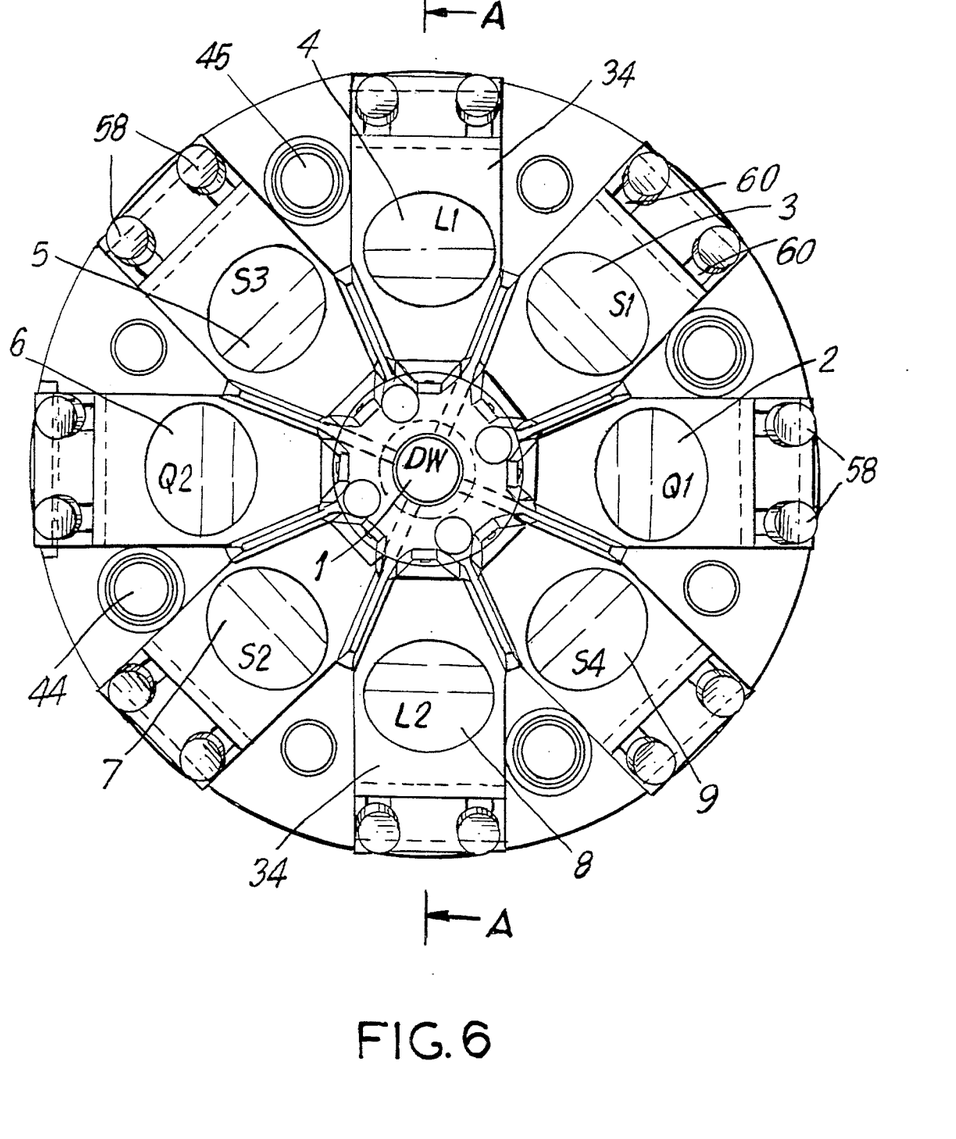
FIG. 6 is a top view of FIG. 5.

Another embodiment example of the test device according to the invention in the arrangement shown schematically in FIG. 2 is shown in FIG. 5 in the same cross section as in FIG. 3 and in the same top view as in FIG. 6. For the sake of simplicity, the same reference numbers are used to designate identical parts. The construction shown in FIG. 5 is suggested so that the sound beam angle in the test device shown in FIG. 3 can continuously change within a broad band width, e.g. 16°–19°. A displaceable displacing plate 54 is arranged below the holding plate 34 and is securely connected with the holding plate 34 via screws 53. The displacing plate 54 is in turn fastened at a surface 59 of the test head carrier via screws 58, which surface 59 is machined in a straight line. As can be seen in the drawing, the fastening screws 58 of the displacing plate 54 are arranged in an elongated hole 60 so that a straight-line displacement of the displacing plate 54 along the machined surface 59 is possible after loosening the screws 58. However, since the common test location 26 should not be changed, the displacement should ideally be effected on a circular path with the common test location 26 as center. However, this would mean a costly spherical machining of the test head carrier 33 and displacing plate 54. To compensate for the deviation brought about by the straight-line displacement, the adjusting system described in FIG. 3 is made use of. The bushing 52 which has already been described and whose end facing the test piece is constructed in a spherical manner is arranged in the holding plate 34. By tightening the screws 53 differently, the occurring deviation can be compensated for again so that the common test location 26 is maintained even in the event of a relatively great change in the sound beam angle. Accordingly, in order to adjust all test heads 2–8 arranged on a circular path, the elongated holes 60 of the displacing plate 54 and the elongated holes 56 for the test heads 2–8 are aligned radially relative to the center of the test head carrier 33.

Figure 7:
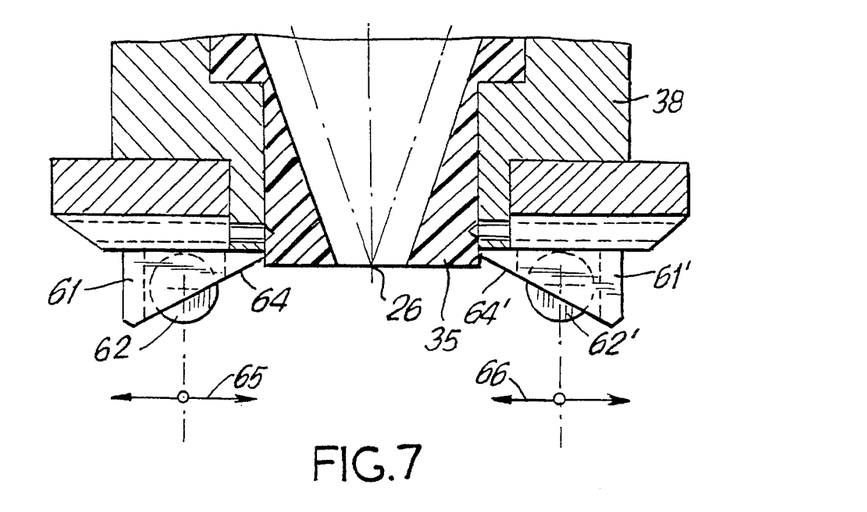
FIG. 7 is a partial cross section through the device in the region of the guide along line A—A in FIG. 8.
Figure 8:
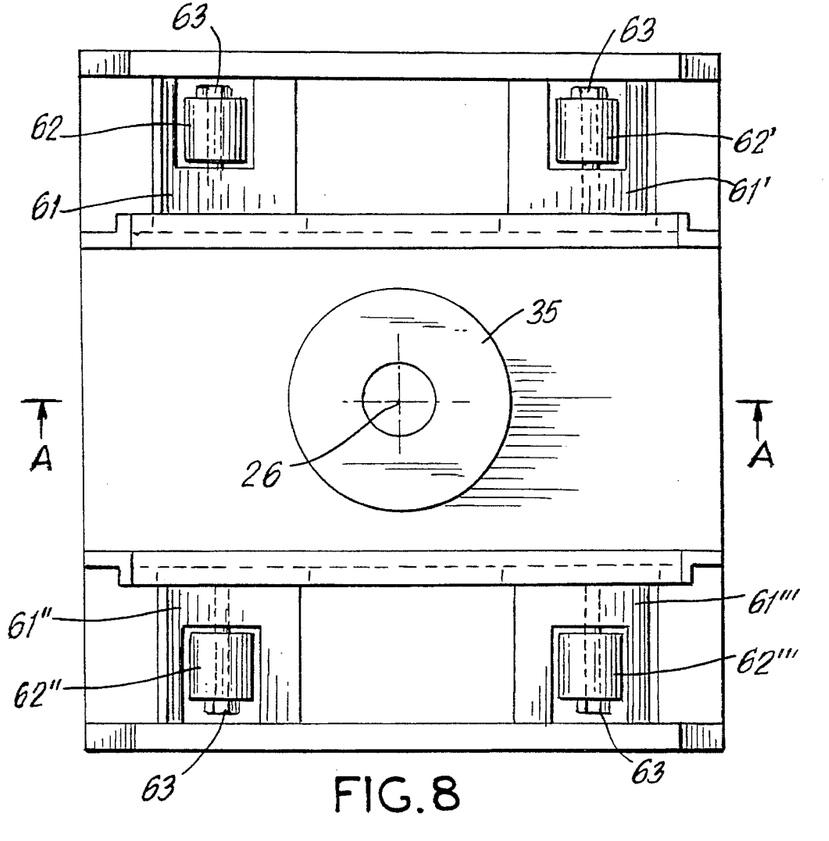
FIG. 8 is a view of FIG. 7 as seen from below.

FIG. 7 shows the lower area of the guide means of the test device, already described, in partial cross section along line A—A of FIG. 8. The pipe 32 to be tested (see FIG. 3) is omitted here for the sake of clarity, but moves in the same manner as was already described with reference to FIG. 3. In contrast to FIG. 3, grooves are cut into the wear bases 61, 61', 61", 61''' and a rolling bearing 62, 62', 62", 62''' is arranged in these grooves in a cantilevering manner. The fastening of the rolling bearing 62, 62', 62", 62''' is effected by means of a screw 63. The dimensions of the groove and rolling bearing 62, 62', 62", 62''' are adapted to one another in such a way that a portion of the outer circumference of the rolling bearing 62, 62', 62", 62''' projects over the surface 64, 64' of the base 61, 61', 61", 61''' facing the pipe 32, not shown. It is accordingly ensured that only the outer surface area of the rolling bearing 62–62''' is in contact with the outer surface area of the pipe 32. Since the rolling bearing 62–62''' is conventionally manufactured from hardened steel, it has a considerably longer useful life than the base 61–61''' which is produced from plastic and accordingly need not be exchanged as frequently. The arrows 65, 66 drawn in below FIG. 7 indicate that the bases 61–61''', including the rolling bearings 62–62''', are displaceable so as to compensate for the different radius of curvature when changing the dimensions of the pipe 32 to be tested. Accordingly, it is ensured that the distance, shown in FIG. 3, to be maintained between the vertex or crest line of the pipe 32 and the outlet point 26 of the chamber 35 remains unchanged.

Figure 9:
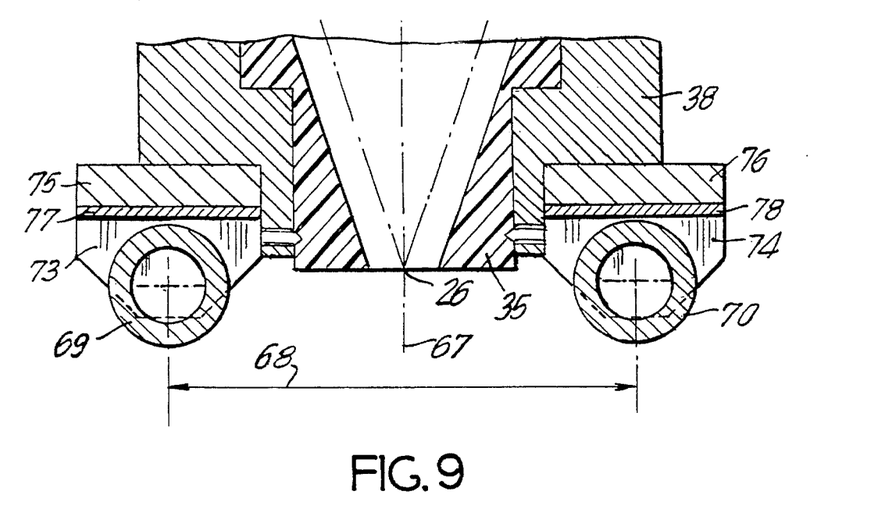
FIG. 9 shows another embodiment form of the invention in the same manner as FIG. 7.
Figure 10:
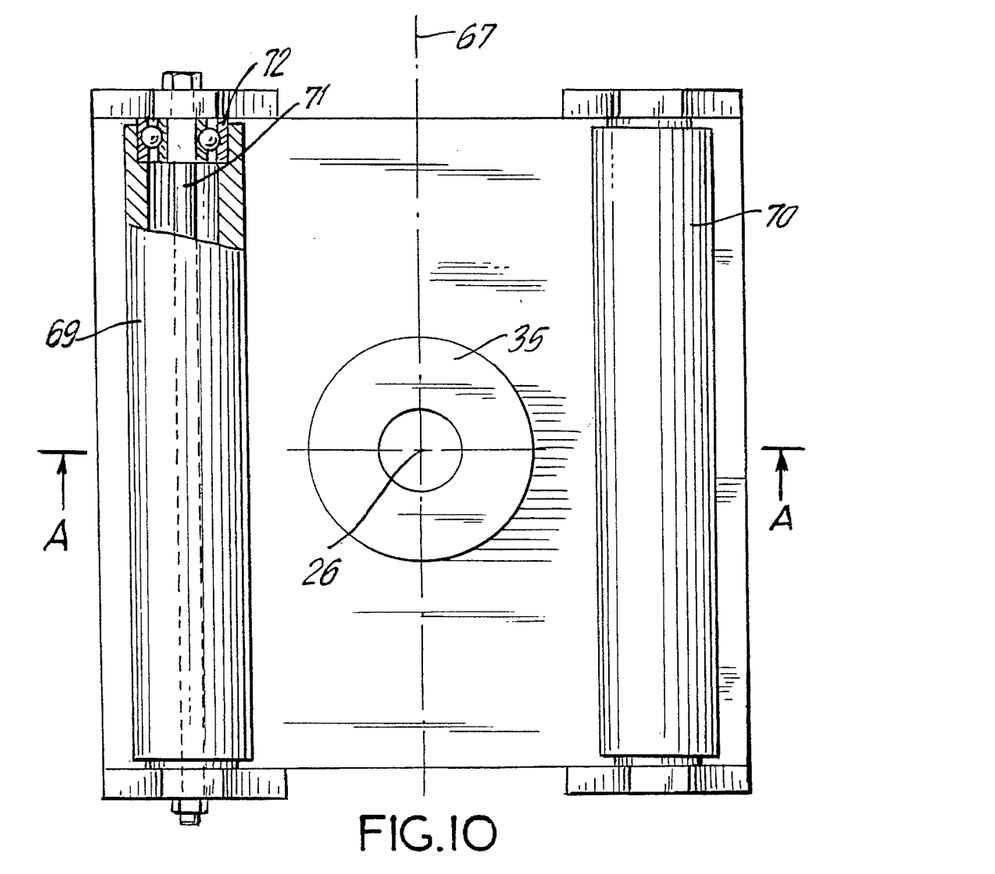
FIG. 10 is a view of FIG. 9 as seen from below.

Another embodiment form of the guidance of the test device is shown in FIGS. 9 and 10 in the same manner as in FIGS. 7 and 8. Instead of the rolls, two rotatably supported rollers 69, 70 are arranged on the right and left sides adjacent to the test axis 67 at a fixed distance 68 from one another. A rod 71 is guided through the hollow roller 69, 70, a roller bearing 72 being arranged at its end. The outer ring of the bearing 72 is supported in a recess of the roller 69. The points of support of the rollers 69, 70 on the pipe 32, not shown here (see FIG. 3), form a triangle together with the test location 26. The height of this triangle depends on the pipe diameter and on the curvature of the outer surface area. An exchangeable intermediate part 77, 78 is arranged between the receiving part 73, 74 for the rollers 69, 70 and the holder 75, 76 so that the distance between the crest line of the pipe to be tested and the test location 26 remains constant when the dimensions are changed. The resulting difference in height can accordingly be compensated for in a simple manner.

Figure 11:
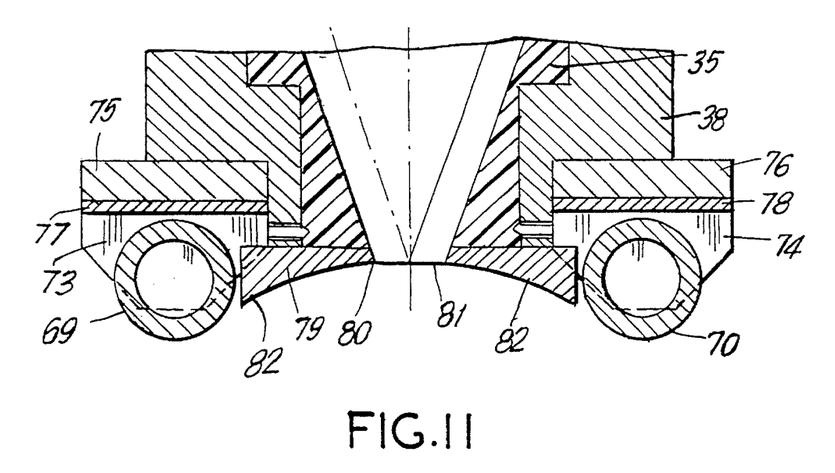
FIG. 11 shows another embodiment form in the same way as FIG. 7.
Figure 12:
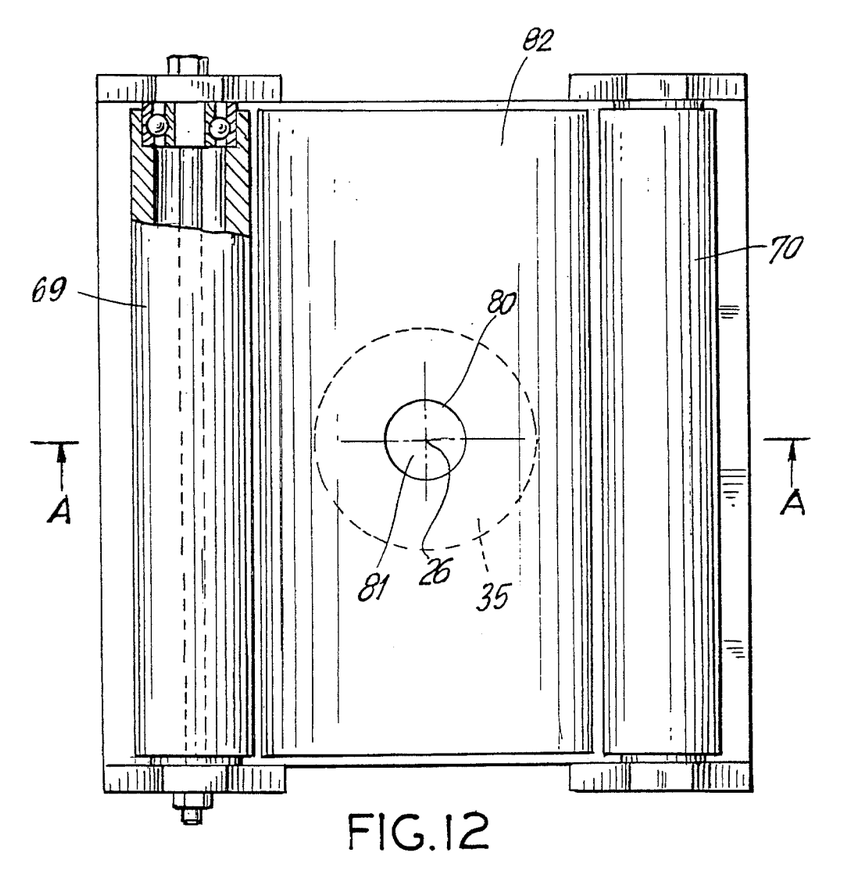
FIG. 12 is a view of FIG. 10 as seen from below.

Another embodiment form is shown in FIGS. 11 and 12. Ideally, in order to achieve a non-contacting guidance, a sickle-shaped member 79 is arranged below the chamber 35 guiding the water. The tips of this member 79 end in a flush manner with the outlet edge 80 of the chamber 35 and enclose the outlet opening 81. The adjoining area of the chamber 35 and the bushing 38 are covered by the member 79.

The surface 82 of the member facing the pipe 32 to be tested (see FIG. 3) is curved in a manner corresponding to the pipe. A narrowly defined gap is accordingly formed between the outer surface of the pipe and the member 79 in which the water exiting from the chamber 35 is guided toward the sides and in the axial direction. The whirling of the exiting water in the edge region of the chamber 35 which would otherwise occur is suppressed by this step. When the pipe 32 to be tested is rotated in a corresponding manner and a corresponding amount of water flows off, a water wedge is formed in the narrow gap so that the test device is guided so as to float without making contact if the surface of the pipe is suitable. The aquaplaning effect is used in this process. When testing hot-finished pipes, the reproducibility of this process is not guaranteed, since the water wedge can collapse suddenly as a result of the rough surface and similar unevenness. In this case, an additional support is required, e.g. by means of rollers 69, 70 as shown in FIG. 11. Alternatively, rolls or conventional wear bases can also be used. In every case, the guides are relieved by the resulting water wedge also when testing hot-finished pipes, so that their useful life is increased.

We claim:

1. An ultrasonic test device for the nondestructive testing of a workpiece moving relative thereto based on the pulse echo method with coupling by means of a fluid medium between the ultrasonic oscillator and the surface of the workpiece, said ultrasonic test device comprising:

a first test head carrier;

at least two test heads disposed in said carrier, each said test head having a sound beam axis, said axes intersecting at a point in the region of the work piece;

a chamber common to all test heads for guiding the fluid medium, said chamber having an outlet opening facing the surface of the workpiece and being connected with said test head carrier;

a guide element constructed so as to correspond to the contour of the workpiece and being connected with said test head carrier; and a separate duct forming a travel path (12–20) associated with each of said test heads (1–9), each said separate travel path having an axis and extending along a determined length of said common chamber, the axis of each of said travel paths being aligned with a respective one said sound beam axis.

2. The ultrasonic test device according to claim 1, further comprising: a second test head carrier (II), including a plurality of test heads immediately adjacent to said first test head carrier (I), the sound beams of said test heads of said first and second test head carriers having, relative to the workpiece, opposite acoustic irradiation directions.

3. The ultrasonic test device according to claim 1, wherein nine test heads (1–9) are arranged in said first test head carrier (33) so that a test head (1) is arranged in the center and eight test heads (2–9) are arranged at a distance to the center test head so as to be symmetrically distributed along a circle at 45° intervals.

4. The ultrasonic test device according to claim 3, wherein said test head (1) arranged in the center is adapted for testing wall thickness and lamination.

5. The ultrasonic test device according to claim 1, additionally comprising:

a test axis (67);

a holder (40, 41) for holding said first test head carrier (33) in the manner of a cardan joint when testing a pipe having an axis;

a guide element having at least two prismatically constructed wear bases (39, 39") arranged to the right and left at the same distance next to said test axis (67) and being adjustable (65, 66) transversely relative to the axis of the pipe (32).

6. The ultrasonic test device according to claim 5, additionally comprising: a rolling bearing (62–62''') having an axis and an outer circumference arranged in said wear base (61–61''') in such a way that said axis of said rolling bearing (62–62''') lies parallel to said axis of the pipe (32) and a portion of said outer circumference projects over said wear surface (64, 64') of said base (61–61''') facing the pipe (32).

7. The ultrasonic test device according to claim 1, additionally comprising:

a test axis (67);

a holder (40, 41) for holding said first stationary said test head carrier (33) in the manner of a cardan joint when testing a pipe having an axis; and a guide element comprising a receiving part (73, 74) and at least two rotatably supported rollers (69, 70) having axes of rotation and being disposed in said receiving part, said rollers (69, 70) being fastened on the right and left sides next to said test axis (67) at a fixed distance (68) from one another, said axes of rotation lying parallel to said axis of the pipe (32) when the pipe (32) moves in a helical line along said stationary test head carrier.

8. The ultrasonic test device according to claim 7, additionally comprising:

a holder (75, 76) for said rollers (69, 70); and an exchangeable intermediate layer (77, 78) arranged between said receiving part (73, 74) and said holder (75, 76).

9. An ultrasonic test device according to claim 1, additionally comprising:

an exchangeable insert (35) defining said travel path, said insert (35) having an outlet edge (80) defining an outlet opening (81) and a surface (82) facing the pipe;

a bushing (38) surrounding said exchangeable insert (35);

a holder (40, 41) for holding said first test head carrier (33) in the manner of a cardan joint when testing a pipe;

a guide element comprising a member (79) having a surface and tips and a sickle-shaped cross section, said tips of the sickle-shaped member being located in the region of said outlet edge (80) of said exchangeable insert (35) and enclosing said outlet opening (81) of said exchangeable insert (35), and said surface (82) facing the pipe (32) being curved corresponding to the outer surface area of the pipe (32);

the region of said exchangeable insert (35) adjoining said outlet opening (81) and said bushing (38) being covered by said sickle-shaped member (79) when the pipe (32) moves in a helical line along said stationary test head carrier (33).

10. The ultrasonic test device according to claim 9, wherein said guide element additionally comprises one of rolls (62–62''') and rollers (67) disposed to the right and left adjacent to said sickle-shaped member (79).

11. The ultrasonic test device according to claim 1, additionally comprising:

a holding plate (34) having a bore hole; and a bushing (52) for guiding said test head (1–9), said bushing (52) being inserted and fixed in said bore hole of said holding plate (34) and having an end, said end of said bushing facing the test piece (32) being constructed so as to be spherical.

12. The ultrasonic test device according to claim 11, wherein said test head carrier (33) has a center and additionally comprising a displacing plate (54) disposed parallel below said holding plate (34), said displacement plate (54) being displacably arranged on said test head carrier (33) and having a bore hole (55) for said test heads (2–8) to pass therethrough, the end of said bore hole (55) facing said holding plate (34) being constructed so as to be spherical, said test head carrier (33) and said displacing plate (54) having elongated holes (56, 60) which are constructed so as to be adapted to a predetermined adjustment path and are aligned radially relative to said center of said test head carrier (33).

\* \* \* \* \*